(12) United States Patent
Bombardelli et al.

(10) Patent No.: US 7,361,370 B2
(45) Date of Patent: Apr. 22, 2008

(54) FORMULATIONS USEFUL IN THE TREATMENT OF MALE AND FEMALE IMPOTENCE

(75) Inventors: Ezio Bombardelli, Milan (IT); Paolo Morazzoni, Milan (IT); Antonella Riva, Milan (IT); Roberto Seghizzi, Milan (IT)

(73) Assignee: Indena S.p.A., Milan (IT)

( * ) Notice: Subject to any disclaimer, the term of this patent is extended or adjusted under 35 U.S.C. 154(b) by 278 days.

(21) Appl. No.: 10/513,819

(22) PCT Filed: May 2, 2003

(86) PCT No.: PCT/EP03/04611

§ 371 (c)(1), (2), (4) Date: Nov. 9, 2004

(87) PCT Pub. No.: WO03/094944

PCT Pub. Date: Nov. 20, 2003

(65) Prior Publication Data

US 2005/0175722 A1 Aug. 11, 2005

(30) Foreign Application Priority Data

May 10, 2002 (IT) .......................... MI2002A0994

(51) Int. Cl.
*A01N 65/00* (2006.01)
(52) U.S. Cl. ...................... 424/725; 424/739
(58) Field of Classification Search ...................... None
See application file for complete search history.

(56) References Cited

U.S. PATENT DOCUMENTS 6,399,579 B1 * 6/2002 Lenoble et al.
6,702,733 B1 * 3/2004 Thompson
6,803,060 B2 * 10/2004 Reyes
2001/0008638 A1 7/2001 Wilding
2002/0013280 A1 1/2002 Xin

FOREIGN PATENT DOCUMENTS

| KR | 2001 009 653 | 2/2001 |
| WO | 00/02573 | 1/2000 |
| WO | 01/11971 | 2/2001 |
| WO | 02/13842 | 2/2002 |

OTHER PUBLICATIONS

P.G. Adaikan et al., "History of herbal medicines with an insight on the pharmacological properties of *Tribulus terrestris*", Aging Male 2001, pp. 163-169 XP009015949.

R.Gjulemetowa et al., "Über Die Bestimmung Von Furostanolsaponinen Im Präparat Tribestan", Pharmazie, vol. 37, No. 4, 1982, p. 296, XP001154500.

Z.L. Sheng et al., "Clinical study of baoyuan dahuang decoction in the treatment of chronic renal failure" Chinese Journal of Integrated Traditional and Western Medicine, China May 1994, vol. 14, No. 5, May 1994 pp. 268-270, 259, XP009016023.

George S. Clark, "Cinnamic Aldehyde", Perfumer & Flavorist, vol. 16, No. 4, Jul. 1991, pp. 26-30, XP009016009.

* cited by examiner

*Primary Examiner*—Michele Flood
(74) *Attorney, Agent, or Firm*—Young & Thompson

(57) ABSTRACT

Pharmaceutical compositions containing: extracts of *Tribulus terrestris*, *Epimedium koreanum*, *Cinnamon cassia* in the weight ratio of 1.5-3.5:1-2:0.1-0.4 respectively; and optionally arginine or a physiologically equivalent ester, salt or precursor thereof. The compositions are useful in the treatment of male and female sexual dysfunctions. A method of treatment using the pharmaceutical compositions is also described.

11 Claims, No Drawings

FORMULATIONS USEFUL IN THE TREATMENT OF MALE AND FEMALE IMPOTENCE

DESCRIPTION OF THE INVENTION

The present invention relates to formulations which are useful in the treatment of male and female sexual dysfunctions.

Sexual dysfunctions have considerable importance, and form the subject of intensive biomedical research efforts. According to recent statistics, the problem of impotence in its various forms (absence of libido and erectile dysfunctions) affects some 70% of the population aged approx. 50 and over. The degree of impotence in its various forms obviously varies in severity, especially among the elderly, where it is often physiologically associated with other disorders such as heart or kidney disease.

The drugs now available to treat such dysfunctions, especially erectile dysfunction, include hormones such as testosterone, VIP, prostaglandin derivatives ($PG_S$), and cardiovascular agents such as papaverine, phenoxybenzamine and phentolamine.

However, none of these drugs provides a satisfactory, permanent solution to the problem, because of the side effects they cause and the need for an intercavernous or intraurethral injection in the case of papaverine and PGE2, for example.

Recently, cGMP phosphodiesterase inhibitors have been developed which are particularly useful in the treatment of impotence, and are active by the oral route. One of these agents, called Sildenafil (WO 94/28902), is already on the market.

Here again, however, the side effects are by no means negligible, and the need for safer and more effective treatments is still strongly felt.

Numerous products of natural origin (mainly plant- but also animal-based) are now being studied by modern pharmacology, on the basis of indications obtained from traditional medicine, to evaluate the possible scientific basis for their empirical use.

Biochemical studies have demonstrated the great complexity of the mechanisms involved in the physiological processes associated with sexual activity, such as penile and clitoral erection, vaginal lubrication, ejaculation and orgasm.

Mediators such as nitric oxide (NO), the enzyme factors involved in the metabolism of the cAMP and cGMP messengers, the adrenergic receptors of the smooth muscle cell membranes, dopaminergic neurotransmitters, and the receptors of $PG_S$ or other hormones are the possible targets of a pharmacological treatment for impotence and other sexual dysfunctions.

It is obviously difficult to provide a satisfactory solution to this specific problem, partly because in addition to the purely biochemical and physiological aspects there are also environmental and psychological factors which can further complicate the clinical picture of patients suffering from sexual disorders.

It has now been found that a combination of extracts of medicinal plants with specific properties, in certain quantity ratios, gives particularly satisfactory therapeutic results in the treatment of male and female sexual dysfunctions.

The invention relates in particular to pharmaceutical compositions comprising:

extracts of *Tribulus terrestris, Epimedium koreanum, Cinnamon cassia* in the weight ratio of 1.5-3.5:1-2:0.1-0.4 respectively;
and optionally
arginine or a physiologically equivalent ester, salt or precursor thereof and a suitable carrier or excipient.

Extracts of *Tribulus terrestris, Epimedium koreanum, Cinnamon cassia* are known and already used in some types of traditional medicine for similar purposes but no association of them are known, especially in the specific quantitative ratios stated above.

In particular, *Tribulus terrestris* extract is known to induce synthesis of testosterone, a hormone responsible for stimulating sexual desire in both men and women; *Epimedium koreanum* extract, which is rich in prenylated flavonoids, has a vasodilating effect mediated by NO release, so that the extract performs a vasokinetic activity on the arteries and arterioles; and *Cinnamon cassia* extract indirectly stimulates the libido by acting on the pleasure-related dopamine receptors.

However, the therapeutic results obtainable with the compositions of the invention cannot be explained solely on the basis of the activity of each extract; in fact, it has surprisingly been found that when the extracts are associated in quantitative ratios different from those stated above, they remain inactive, and can even aggravate the disorder. A real increase in sexual activity can therefore only be obtained by using the extracts of the various plants in a precise ratio which increases both libido and the blood supply to the genital organs.

The weight ratio of extracts of *Tribulus terrestris, Epimedium koreanum* and *Cinnamon cassia* is preferably 2.5:1.5:0.2.

Arginine, its salt, ester or precursor, when used, is present in a quantitative ratio of between 0.5 and 1.5, preferably 1, to the plant extracts.

Extracts of the medicinal plants specified above, obtained by conventional techniques such as extraction with solvents or supercritical fluids, can be used for the purposes of this invention.

However, the use of standardised extracts with a predetermined content of certain characteristic components of the extract is preferred: for example, *Tribulus terrestris* extract will contain approx. 40% of saponins expressed as dioscin; *Epimedium koreanum* extract is preferably an extract with a flavonoid content (expressed as ikarine) of approx. 60%; and *Cinnamon cassia* extract preferably has a cinnamic aldehyde content of approx. 70%.

When preparing the extracts, various parts of the plants can be used, as they contain the active constituents in different concentrations.

The whole plant is used to prepare *Epimedium koreanum* extracts in particular; *Tribulus terrestris* extracts are preferably obtained from the aerial parts and seeds of the plant. In both cases, the extraction is preferably carried out with a 40% ethanol/water mixture, at temperatures of 25-85° C., preferably at 50° C.

*Cinnamon cassia* extracts are preferably prepared by extraction from the bark of the trunk with carbon dioxide under supercritical pressure conditions of between 150 and 300 bars, preferably at 210 bars.

The extracts of *Tribulus* and *Epimedium* can be further enriched in active principles by back-extraction of the concentrated aqueous extracts with water-immiscible solvents, which extract with sufficient selectivity either the flavonoids or the saponins, respectively. Suitable water immiscible or partially miscible solvents are preferably ethyl acetate or n-butanol; the solvents used, after drying, are concentrated to dryness or to small volume, diluted with aprotic solvents such as aliphatic ethers or aliphatic or aromatic hydrocarbons, in which the active principles are insoluble. Precipitation of the active principles in aprotic solvents allows to remove undesired inert substances and to concentrate the active principles.

The purification of the extract of *Cinnamon cassia* is not necessary, as the extraction system is sufficiently selective.

The invention also relates to the use of extracts of *Tribulus terrestris, Epimedium koreanum* and *Cinnamon cassia* in the weight ratio of 1.5-3.5:1-2:0.1-0.4 respectively, and optionally arginine or a physiologically equivalent esters, salts or precursors thereof, to prepare medicaments for the treatment of male and female sexual dysfunctions, and especially for the treatment of impotence, erectile dysfunctions, libido disorders, frigidity and anorgasmia.

As an alternative to the plant extracts, the corresponding isolated active ingredients may be used, particularly a combination of dioscin, ikarin and cinnamic aldehyde. The use of said combination for the preparation of a medicament for the treatment of impotence, erectile dysfunction, libido disorders, frigidity and anorgasmia as well as the medicaments comprising said combination are further objects of the invention.

The mixture of extracts of the invention must be taken chronically, not just immediately before sexual intercourse, although in some individuals the response takes place on the first treatment, within 30 minutes of taking the drug.

Chronic administration of the compositions of the invention does not cause any significant side effects, is well tolerated, and does not alter the delicate hormone balances, especially the androgen/oestrogen balance, which govern major physiological events in men and women such as the andropause and the menopause.

Examples of suitable forms of administration of the compositions of the invention include tablets, soft and hard gelatin capsules, suppositories and drinkable preparations containing unit doses of between 100 and 300 mg of *Tribulus terrestris* extract and unit doses of the other components in accordance with the weight ratios specified above. Solid-phase formulations such as unmodified-release or gastroresistant tablets or drinkable liquid forms are particularly preferred.

The following examples are given to illustrate the invention rather than to limit its scope.

EXAMPLE 1

Preparation of Coated Tablets

| Each 700 mg coated tablet contains: | |
|---|---|
| *Tribulus terrestris* | 250.00 mg |
| *Epimedium koreanum* | 150.00 mg |
| *Cinnamon cassia* | 20.00 mg |
| L-arginine | 100.00 mg |
| Soya polysaccharides | 55.00 mg |
| Silicon dioxide | 14.00 mg |
| Silicified microcrystalline cellulose | 92.00 mg |
| Magnesium stearate | 4.00 mg |
| Hydroxypropyl methylcellulose | 6.40 mg |
| Talc | 5.20 mg |
| Titanium dioxide | 2.00 mg |
| Glycerin | 0.12 mg |
| Polysorbate 80 | 0.80 mg |
| Quinoline | 0.43 mg |
| Indigotine | 0.05 mg |

EXAMPLE 2

Preparation of Hard Gelatin Capsules

| Each 340 mg capsule contains: | |
|---|---|
| *Tribulus terrestris* | 125.00 mg |
| *Epimedium koreanum* | 75.00 mg |
| *Cinnamon cassia* | 10.00 mg |
| L-arginine | 50.00 mg |
| Soya polysaccharides | 25.00 mg |
| Silicon dioxide | 7.00 mg |
| Silicified microcrystalline cellulose | 45.00 mg |
| Magnesium stearate | 1.50 mg |
| Talc | 1.50 mg |

EXAMPLE 3

Preparation of Soft Gelatin Capsules

| Each 700 mg soft gelatin capsule contains: | |
|---|---|
| *Tribulus terrestris* | 125.00 mg |
| *Epimedium koreanum* | 75.00 mg |
| *Cinnamon cassia* | 10.00 mg |
| L-Arginine | 50.00 mg |
| Soya lecithin | 20.00 mg |
| Medium-chain triglycerides | 100.00 mg |
| Polysorbate 80 | 10.00 mg |
| Soya oil | 300.00 mg |
| Colloidal silicon dioxide | 10.00 mg |

EXAMPLE 4

Preparation of a Drinkable Solution

| Each 10 mL vial contains: | |
|---|---|
| *Tribulus terrestris* | 250.00 mg |
| *Epimedium koreanum* | 150.00 mg |
| *Cinnamon cassia* | 20.00 mg |
| L-arginine hydrochloride | 100.00 mg |
| Glycerin | 3000.00 mg |
| Polysorbate 20 | 800.00 mg |
| Propylene glycol | 1000.00 mg |
| Acesulfame K | 175.00 mg |
| Sodium saccharine | 40.00 mg |
| Neohesperidine DC | 2.50 mg |
| Flavouring | 300.00 mg |
| Potassium sorbate | 11.70 mg |
| Methyl paraben | 8.30 mg |
| Purified water | q.s. to 10.00 mL |

EXAMPLE 5

Preparation of a Soluble Granulate

| Each 5000 mg sachet contains: | |
| --- | --- |
| Tribulus terrestris | 250.00 mg |
| Epimedium koreanum | 150.00 mg |
| Cinnamon cassia | 20.00 mg |
| L-arginine hydrochloride | 100.00 mg |
| Polysorbate 20 | 500.00 mg |
| Acesulfame K | 175.00 mg |
| Sodium saccharine | 40.00 mg |
| Neohesperidine DC | 2.50 mg |
| Flavouring | 300.00 mg |
| Inulin | 1000.00 mg |
| Mannitol | 2412.50 mg |

The invention claimed is:

1. A pharmaceutical composition comprising:
an extract of *Tribulus terrestris*,
an extract of *Epimedium koreanum*, and
an extract of *Cinnamon cassia*, and wherein the extract of *Tribulus terrestris*, extract of *Epimedium koreanum*, and extract of *Cinnamon cassia* are in a weight ratio of 1.5-3.5:1-2:0.1-0.4, respectively;
and a suitable carrier or excipient.

2. The composition as claimed in claim 1, wherein the weight ratio of the extract of *Tribulus terrestris*, extract of *Epimedium koreanum* and extract of *Cinnamon cassia* are 2.5:1.5:0.2.

3. The composition as claimed in claim 1, further comprising L-arginine or L-arginine hydrochloride.

4. The composition as claimed in claim 3, wherein the weight ratio of the extract of *Tribulus terrestris*, extract of *Epimedium koreanum*, extract of *Cinnamon cassia* and L-arginine or L-arginine hydrochloride is 2.5:1.5:0.2:1.

5. The composition as claimed in claim 3, containing *Tribulus terrestris*, an extract of *Epimedium koreanum*, an extract of *Cinnamon cassia* extracts and L-arginine or L arginine hydrochloride respectively in weight ratios of 1.5-3.5:1-2:0.1-0.4:0.5-1.5.

6. A composition comprising:
an extract of *Tribulus terrestris*,
an extract of *Epimedium koreanum*, and
an extract of *Cinnamon cassia*, and
wherein the extract of *Tribulus terrestris*, extract of *Epimedium koreanum*, and extract of *Cinnamon cassia* are in a weight ratio of 1.5-3.5:1-2:0.1-0.4, respectively.

7. The composition as claimed in claim 6, wherein the weight ratio of the extract of *Tribulus terrestris*, extract of *Epimedium koreanum* and extract of *Cinnamon cassia* are 2.5:1.5:0.2.

8. The composition as claimed in claim 6, further comprising L-arginine or L-arginine hydrochloride, wherein the extract of *Tribulus terrestris*; extract of *Epimedium koreanum*; extract of *Cinnamon cassia*; and L-arginine or L-arginine hydrochloride are in weight ratios of 1.5-3.5:1-2:0.1-0.4:0.5-1.5.

9. The composition as claimed in claim 7, wherein the weight ratio of the extract of *Tribulus terrestris*, extract of *Epimedium koreanum*, extract of *Cinnamon cassia* and L-arginine or L-arginine hydrochloride is 2.5:1.5:0.2:1.

10. The composition according to claim 6, further comprising arginine or a physiologically equivalent ester or salt.

11. The composition according to claim 1, further comprising arginine or a physiologically equivalent ester or salt.

* * * * *